(12) United States Patent
Skoog

(10) Patent No.: US 8,257,412 B1
(45) Date of Patent: Sep. 4, 2012

(54) THERAPY DEVICE HOLDING SYSTEM

(76) Inventor: Thomas K. Skoog, Rapid City, SD (US)

( * ) Notice: Subject to any disclaimer, the term of this patent is extended or adjusted under 35 U.S.C. 154(b) by 200 days.

(21) Appl. No.: 12/837,831

(22) Filed: Jul. 16, 2010

(51) Int. Cl.
*A61N 5/06* (2006.01)
(52) U.S. Cl. ............... 607/89; 607/88; 606/19; 606/13
(58) Field of Classification Search ............ 607/89, 607/88; 606/19, 13
See application file for complete search history.

(56) References Cited

U.S. PATENT DOCUMENTS

| | | | |
|---|---|---|---|
| 4,231,603 A | 11/1980 | Van Zelm | |
| 4,374,600 A | 2/1983 | Van Zelm | |
| 4,711,482 A | 12/1987 | Brown | |
| 5,205,598 A | 4/1993 | Miller | |
| 5,647,622 A | 7/1997 | Schectman | |
| 5,895,082 A | 4/1999 | Kaluzny | |
| 5,950,315 A | 9/1999 | Linden | |
| 6,267,735 B1 * | 7/2001 | Blanchard et al. | 601/33 |
| 6,669,254 B2 | 12/2003 | Thom | |
| 6,874,833 B2 | 4/2005 | Keith | |
| 2003/0199946 A1 * | 10/2003 | Gutwein | 607/88 |
| 2007/0046049 A1 | 3/2007 | Gale | |
| 2009/0159487 A1 | 6/2009 | Tacoma | |
| 2010/0324357 A1 * | 12/2010 | Chu | 600/37 |

* cited by examiner

*Primary Examiner* — Kinam Park
(74) *Attorney, Agent, or Firm* — Jeffrey A. Proehl; Woods, Fuller, Shultz & Smith, P.C.

(57) ABSTRACT

A reach extending device for extending the reach and effective positioning of a therapy device comprises a holder portion configured to grip a therapy device and a handle portion releasbly mounted on the holder portion. The holder portion comprises a mounting element removably mountable on the handle portion, and a movable element for removably mounting on the therapy device. The movable element may be movably mounted on the mounting element to permit movement of the movable element with respect to the handle portion. The handle portion comprises at least two sections, and includes a base section and at least one extension section extendable from the base section. The at least one extension section may be movable between a retracted position and an extended position.

18 Claims, 9 Drawing Sheets

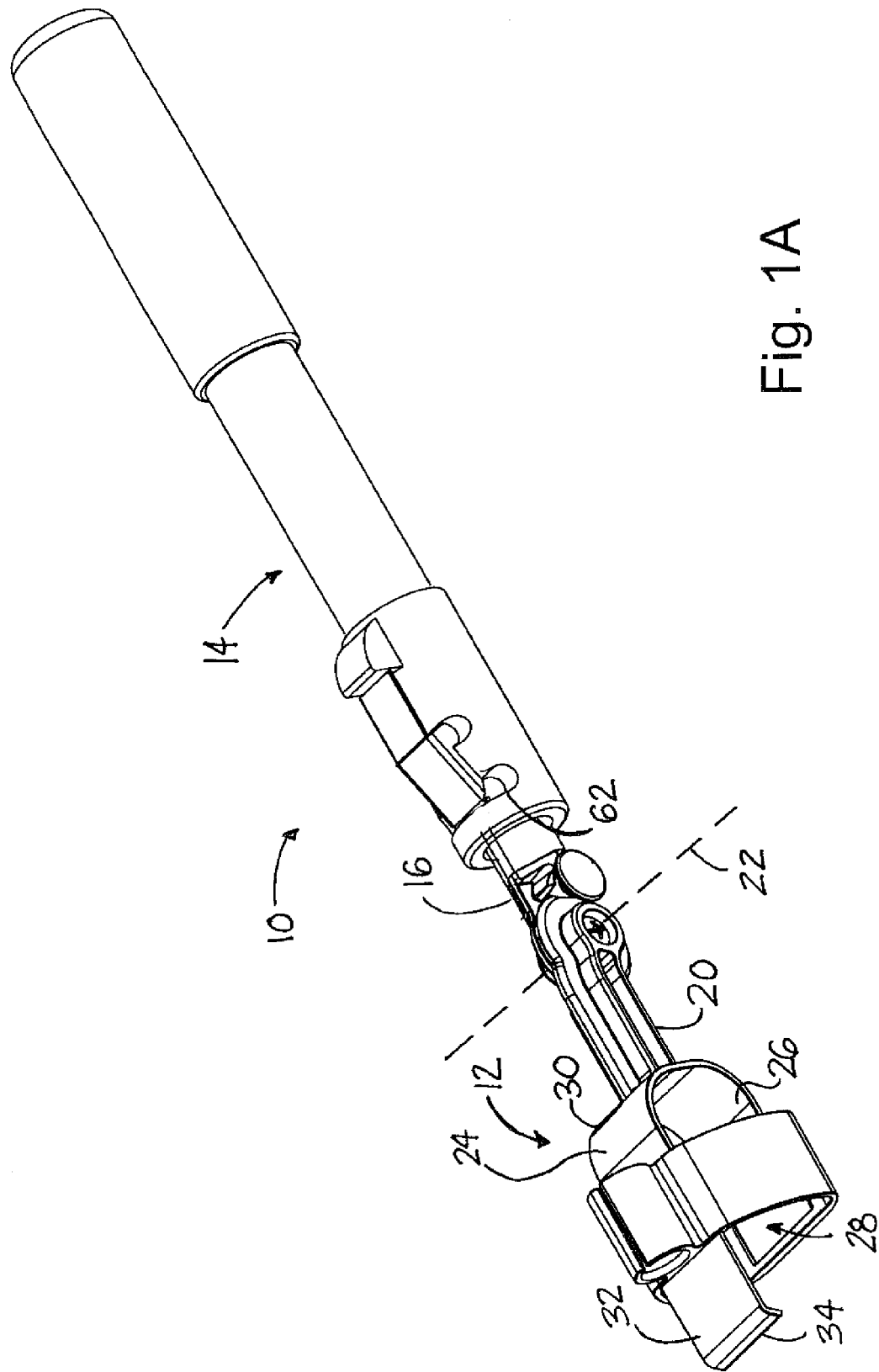

THERAPY DEVICE HOLDING SYSTEM

BACKGROUND

1. Field

The present disclosure relates to device holders and more particularly pertains to a new therapy device holding system for extending the reach and effective positioning of a therapy device by a user.

2. Summary

The present disclosure describes a new therapy device holding system which may be utilized for extending the reach and effective positioning of a therapy device by a user.

In one aspect, the present disclosure relates to a reach extending device for extending the reach and effective positioning of a therapy device. The reach extending device may comprise a holder portion configured to grip a therapy device and a handle portion releasably mounted on the holder portion. The holder portion may comprise a mounting element removably mountable on the handle portion, and a movable element for removably mounting on the therapy device. The movable element may be movably mounted on the mounting element to permit movement of the movable element with respect to the handle portion. The handle portion may comprise at least two sections, including a base section and at least one extension section extendable from the base section. The at least one extension section may be movable between a retracted position and an extended position.

In another aspect, the disclosure relates to a therapy system that may comprise a therapy device having a housing with a first end and a second end. The system may also comprise a reach extending device comprising a holder portion receiving at least a portion of the housing of the therapy device, and a handle portion releasbly mounted on the holder portion. The holder portion may comprise a mounting element removably mountable on the handle portion, and a movable element removably receiving the therapy device. The movable element may be movably mounted on the mounting element to permit movement of the therapy device with respect to the handle portion. The handle portion may comprise at least two sections, including a base section and at least one extension section extendable from the base section. The at least one extension section may be movable between a retracted position and an extended position.

In yet another aspect of the disclosure, a reach extending device for extending the reach and effective positioning of a therapy device that may comprise a holder portion configured to grip a therapy device and a handle portion releasbly mounted on the holder portion. The holder portion may comprise a mounting element removably mountable on the handle portion, and a movable element for removably mounting on the therapy device. The movable element may be movably mounted on the mounting element to permit movement of the movable element with respect to the handle portion. The handle portion may comprise at least two sections, including a base section and at least one extension section extendable from the base section. The at least one extension section may be movable between a retracted position and an extended position. The holder portion may comprise an engaging structure configured to releasably lock a position of the movable element with respect to the mounting element.

There has thus been outlined, rather broadly, some of the more important elements of the invention in order that the detailed description thereof that follows may be better understood, and in order that the present contribution to the art may be better appreciated. There are additional elements of the invention that will be described hereinafter and which will form the subject matter of the claims appended hereto.

In this respect, before explaining at least one embodiment or implementation in greater detail, it is to be understood that the scope of the invention is not limited in its application to the details of construction and to the arrangements of the components set forth in the following description or illustrated in the drawings. The invention is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present invention.

The advantages of the various embodiments of the present invention, along with the various features of novelty that characterize the invention, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein:

FIG. 1A is a schematic perspective view of a reach extending device of the new therapy device holding system according to the present disclosure, particularly showing the handle portion in a retracted position.

DETAILED DESCRIPTION

Figure 1B:
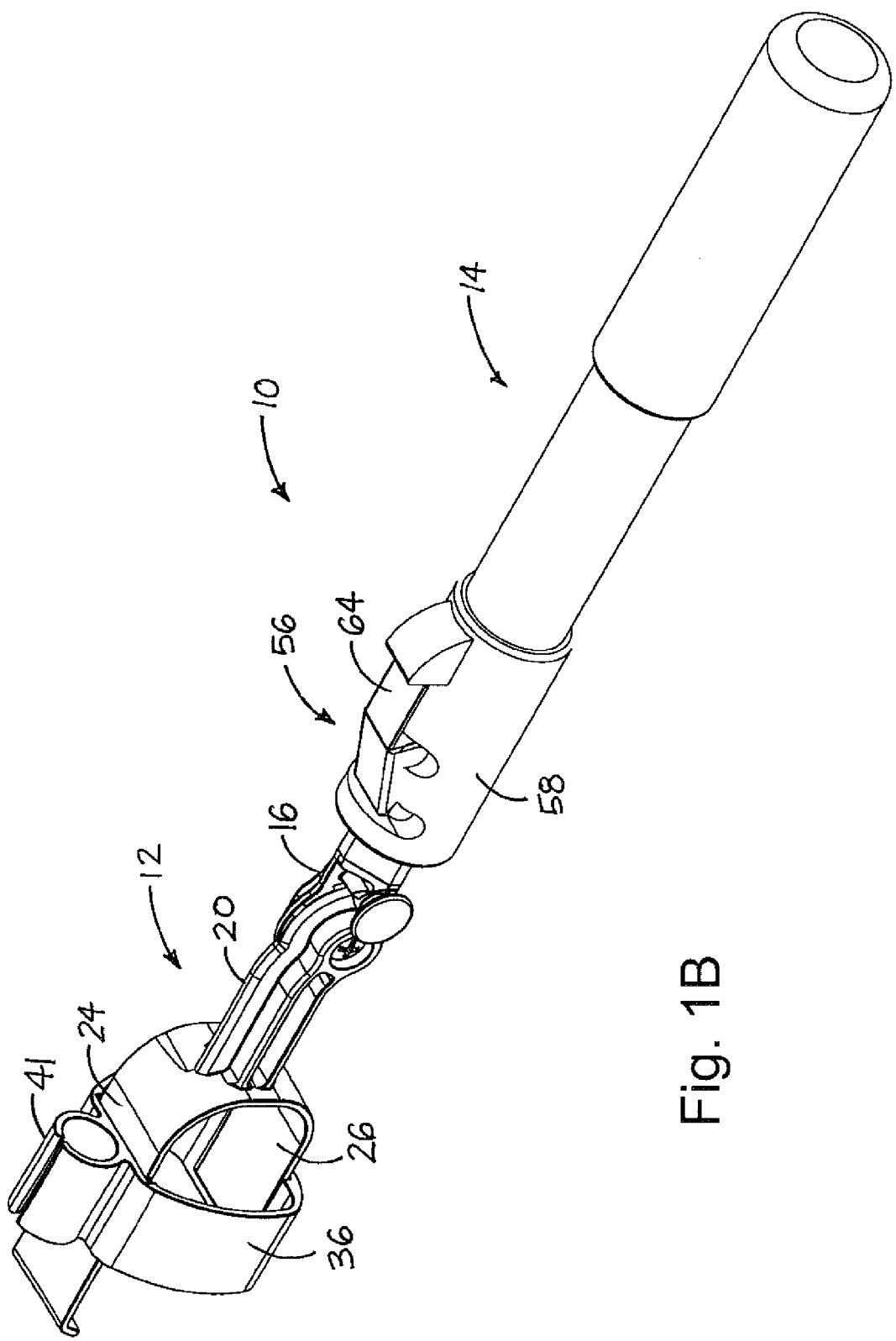
FIG. 1B is a schematic perspective view of the reach extending device according to the present disclosure and shown at a reverse angle from FIG. 1A.
Figure 2A:
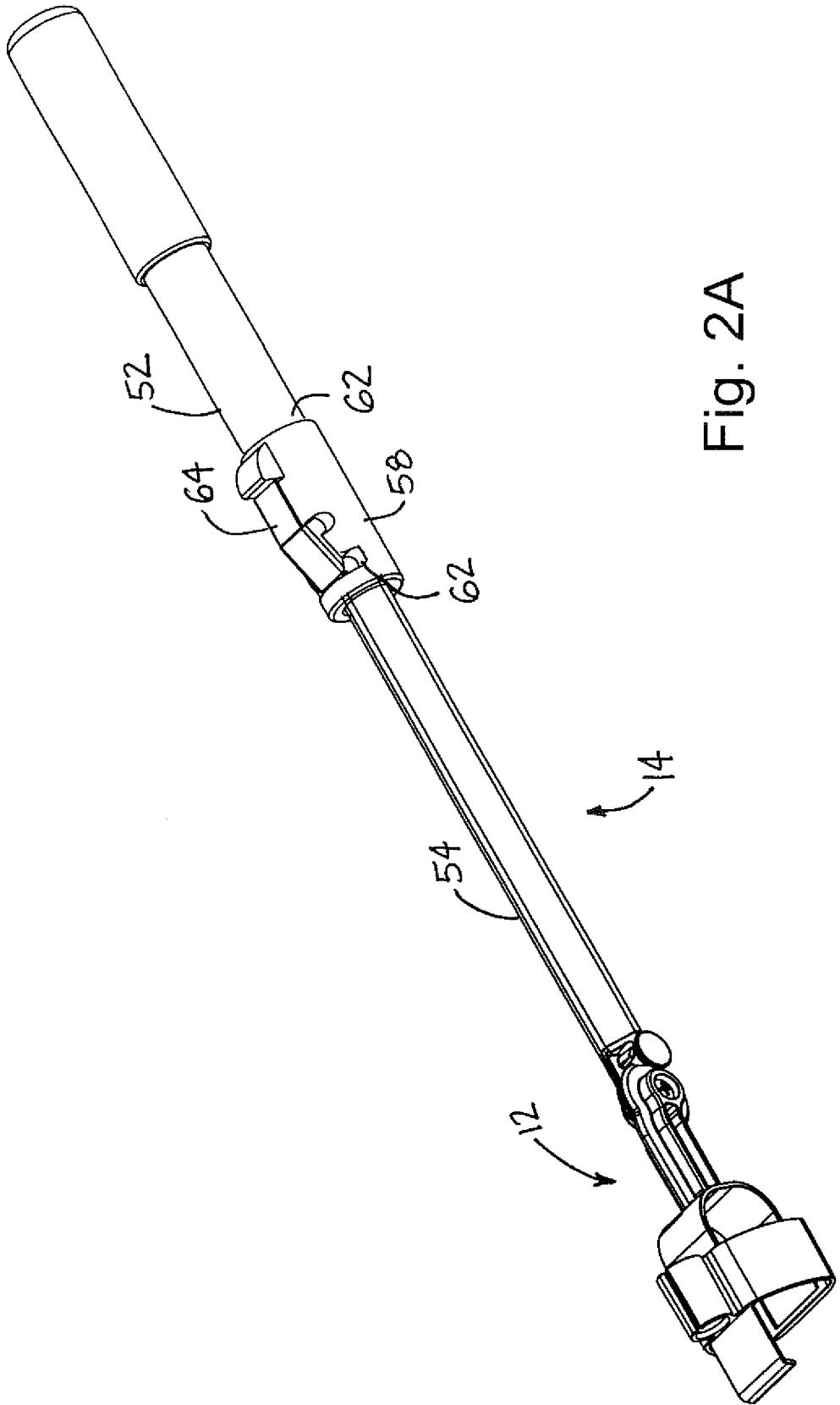
FIG. 2A is a schematic perspective view of the reach extending device, according to an illustrative embodiment, particularly showing the handle portion in an extended position.
Figure 2B:
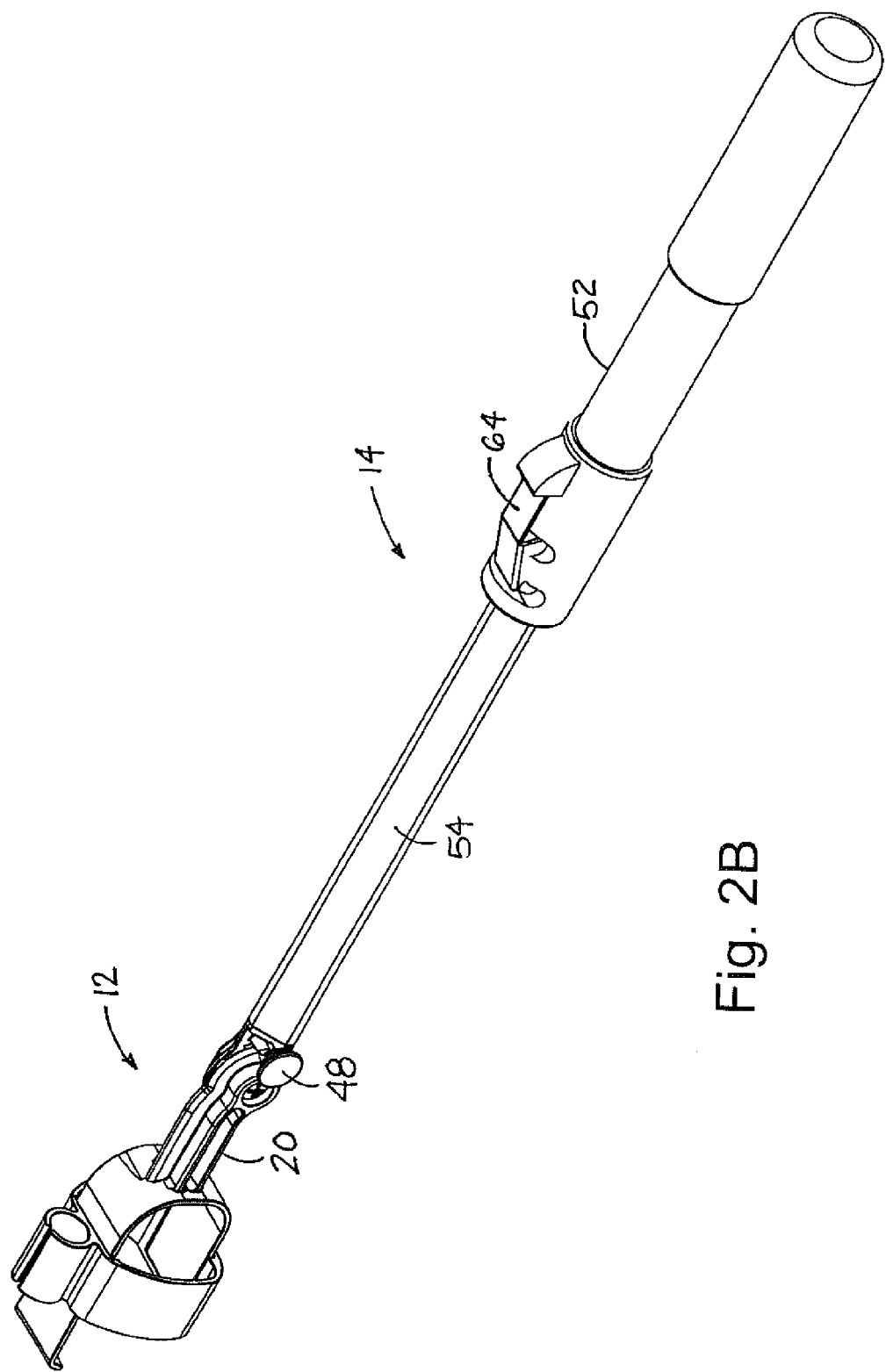
FIG. 2B is a schematic perspective view of the reach extending device, according to an illustrative embodiment, and shown at a reverse angle from FIG. 2A.
Figure 3:
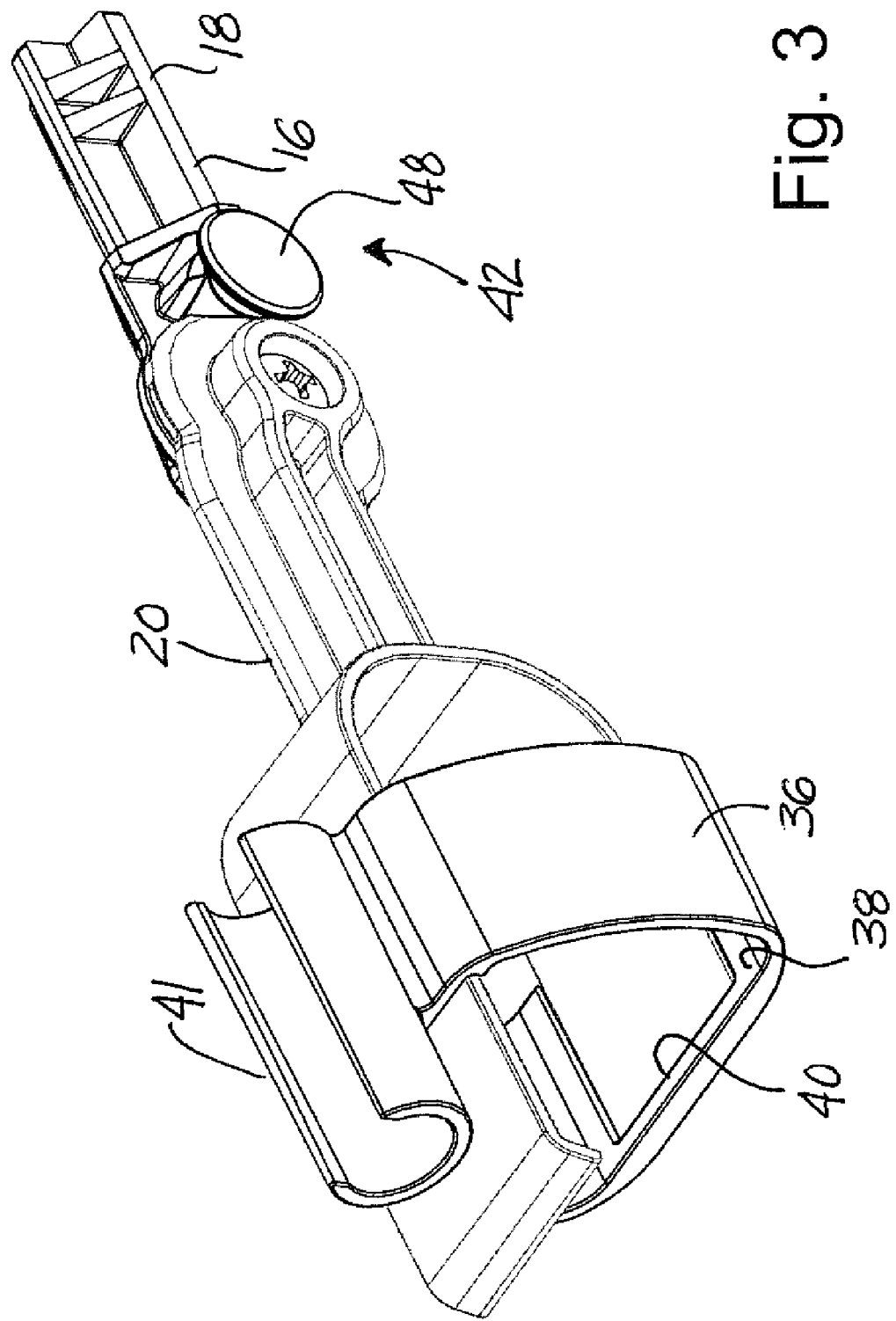
FIG. 3 is a schematic perspective view of the holder portion of the reach extending device, according to an illustrative embodiment.
Figure 4:
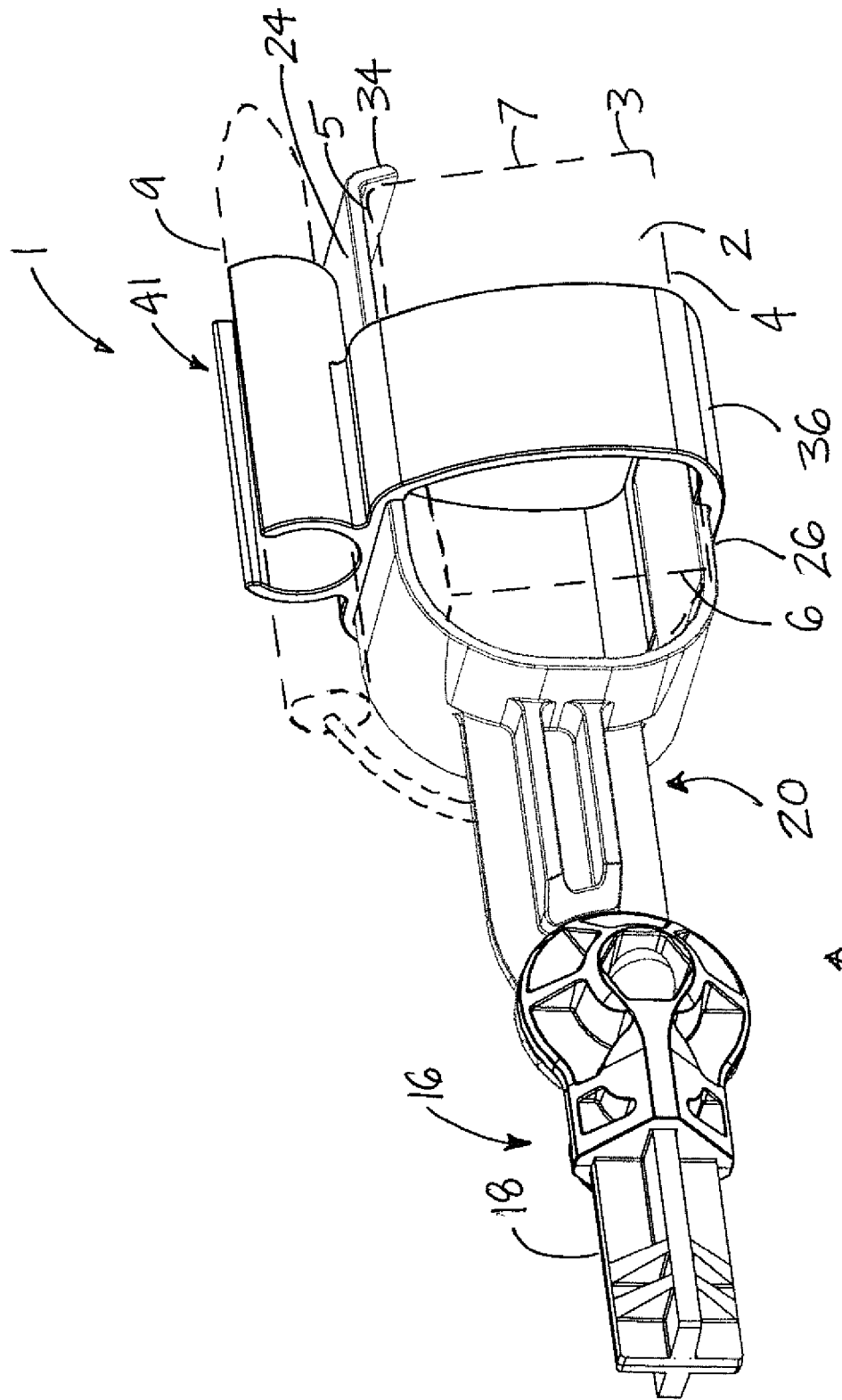
FIG. 4 is a schematic perspective view of the holder portion of the reach extending device with a therapy device mounted thereon, according to an illustrative embodiment.
Figure 5:
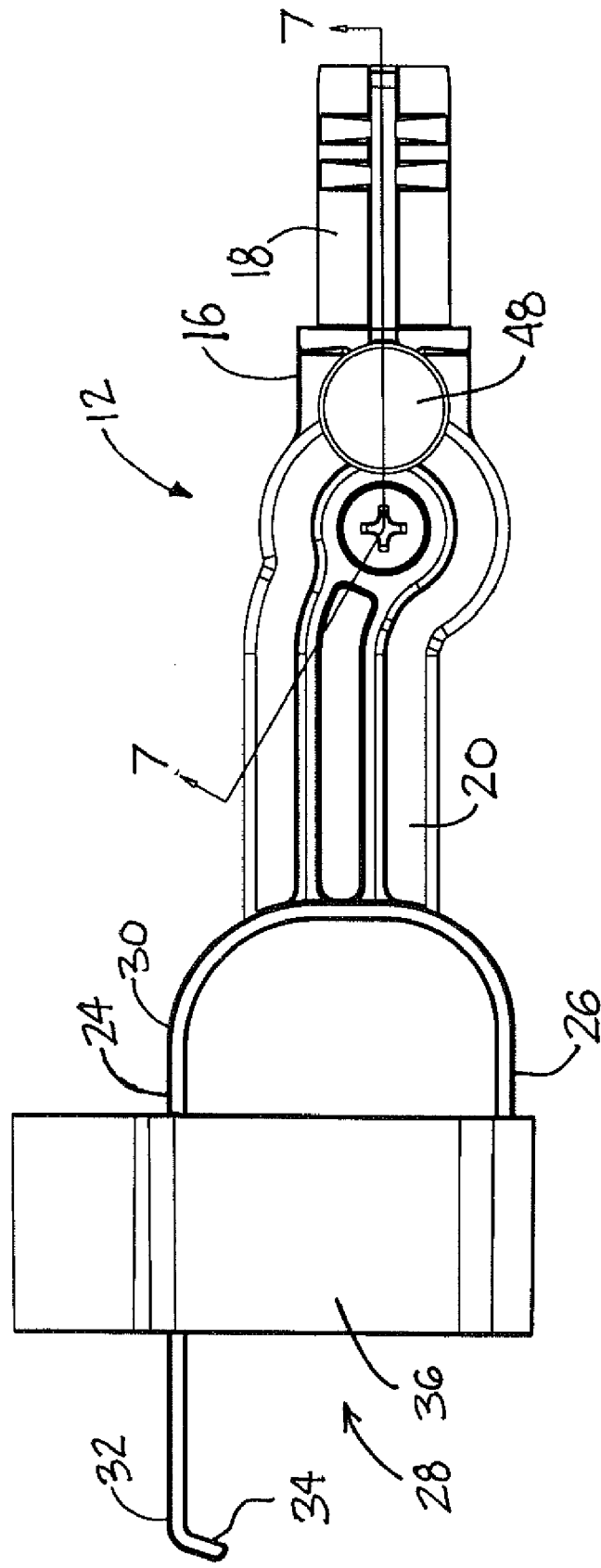
FIG. 5 is a schematic side view of the holder portion of the reach extending device with the retaining loop element, according to an illustrative embodiment.
Figure 6:
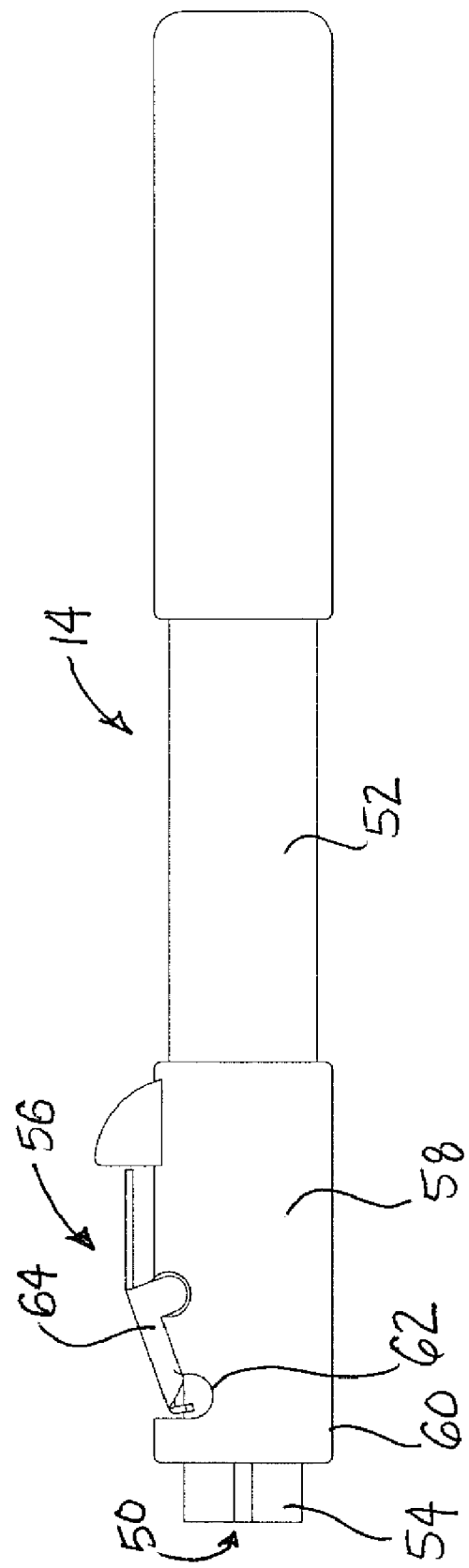
FIG. 6 is a schematic side view of the handle portion, according to an illustrative embodiment.
Figure 7:
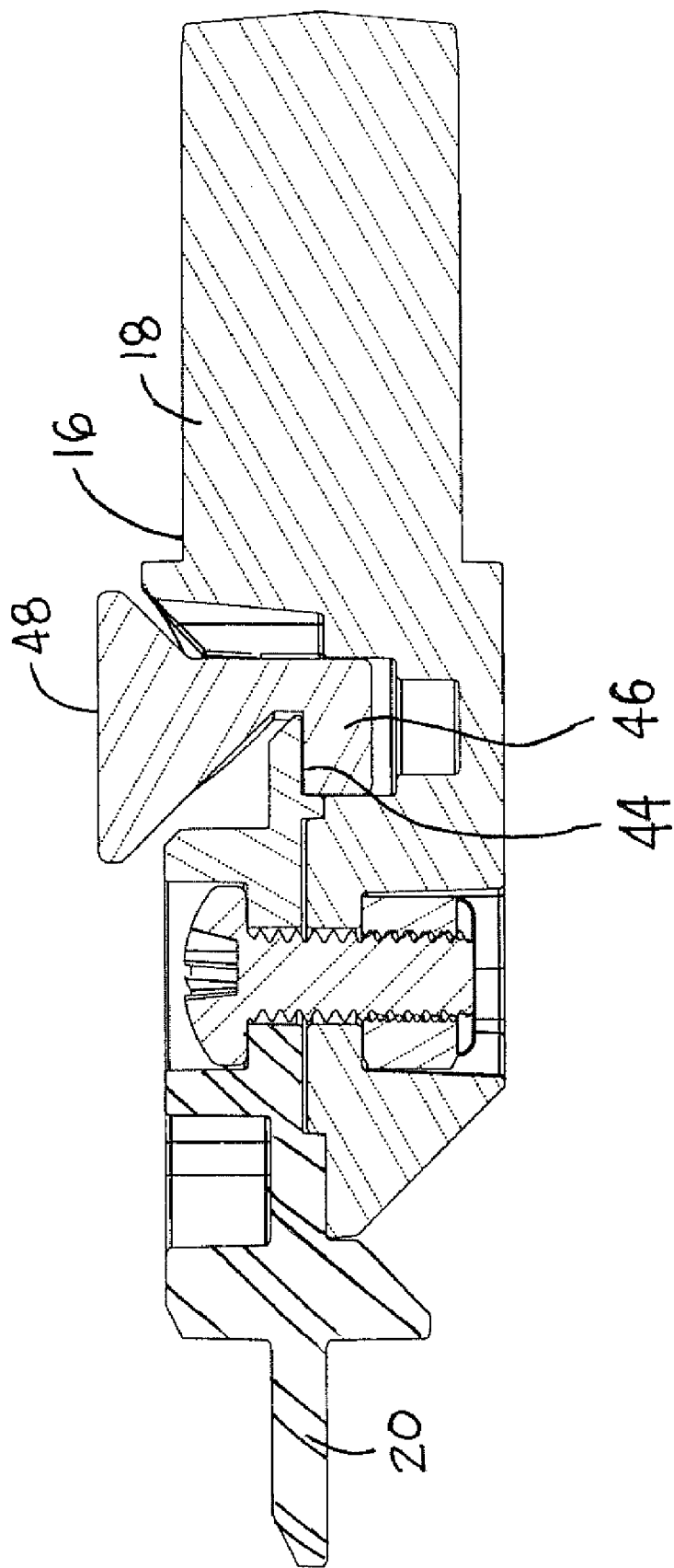
FIG. 7 is a schematic sectional view of the engaging structure of the mounting and movable elements of the holder portion taken along line 7-7 in FIG. 5.

With reference now to the drawings, and in particular to FIGS. 1 through 7 thereof, a new therapy device holding system embodying the principles and concepts of the disclosed subject matter will be described.

The therapy device holding system 10 is highly suitable as a part of a therapy system 1 that utilizes a laser therapy device 2 that may be employed to apply laser radiation or energy to parts of the body that would benefit from such treatment. The therapy device 2 is typically designed for being hand held by the user to support the device in the proper orientation to expose a part of the body with laser energy emitted from the device. However, various portion of the body may not be reachable with the laser energy when the user holds the device 2 in his or her hand, thus limiting the portion of the body that may be effectively treated, especially in those persons whose mobility and flexibility may be limited by the condition that they are attempting to treat with the therapy device.

In general, the laser therapy device 2 (and similar therapeutic devices) may have a housing 3 which may be characterized by having a front 4 and a rear 5, as well as a first end 6 and a second end 7. The second end 7 may be located opposite of the first end 6, and in some embodiments the second end may be characterized by laser energy being emitted from the second end when the device 2 is powered on and being operated for therapeutic purposes. In other embodiments, separate probe 9 may be electrically connected to the housing of the therapy device 2 and may have the actual laser emission circuitry.

The present disclosure relates to a reach extending device 10 that, in a broad sense, functions to extend the reach of the user's arm or arms for more effective positioning of the therapy device 2 by the user of the device 2 as the user holds onto the reach extending device 10. In a general sense, the reach extending device 10 may comprise a holder portion 12 that may be adapted to grip a device such as the laser therapy device 2, and may also include a handle portion 14 that mounts to the holder portion to extend and enhance the effective reach of the user. The holder portion 12 may be removably mounted on the handle portion 14 to allow for interchangeability of different holder portions, configured to fit different laser treatment devices, and different handle portions, configured with different lengths and degrees of adjustability.

In greater detail, the holder portion 12 may comprise a mounting element 16 that may be removably mountable on the handle portion 14, although a more permanent mounting may be utilized. The mounting element 16 may comprise a bayonet structure 18 that has an end portion that tapers in size to some degree toward the end of the end portion. The holder portion may further comprise a movable element 20 that may be mounted on the mounting element 16 for movement with respect to the mounting element. In some embodiments, the movable element 20 may be pivotable about a pivot axis 22 with respect to the mounting element 16.

The movable element 16 may include a pair of opposed elements 24, 26 that are configured for positioning on opposite sides (e.g., the front and rear) of the housing 3 of the laser treatment device. The opposed elements 24, 26 may have a U-shaped configuration may be spaced from each other to define a gap 28 for receiving the therapy device 2. The pair of opposed elements may include a first arm 24, and the first arm may have a proximal end 30 and a distal end 32. A lip 34 may be formed on the distal end for engaging the housing of the therapy device to assist in holding the device in the holder portion, and the lip may extend along a width of the distal end. The pair of opposed elements may also include a second arm 26 which may extend substantially parallel to the first arm 24. The length of the second arm 26 may be shorter that the length of the first arm, although the arms may be configured in different ways for engaging housings of different brands and manufacturers of the therapy device.

A retaining loop element 36 may be employed as a part of the movable element 20 and may be positionable about the first 24 and second 26 arms. The retaining loop element 36 may engage the first 24 and second 26 arms to restrict movement of the arms away from each other. The loop element 36 may encompass the arms 24, 26 to restrict their outward movement with respect to each other. The retaining loop 36 may have an inward surface 38, and the inward surface may define a pocket 40 that is configured to receive an end of the second arm to assist in locating the loop element on the arms, and the retaining loop may be united to the first and second arms. The retaining loop element 36 may include a probe mounting structure 41 for removably mounting a laser energy emitting probe on the loop element and the holder portion in proximity to the laser therapy device that may be positioned between the opposed elements 24, 26 of the holder portion. The probe mounting structure 41 may comprise a pair of spaced ears that are positionable on opposite sides of the probe, and may have curved inward surfaces for engaging a portion of the exterior of the probe, which in many cases will have a substantially cylindrical exterior shape resembling a pen. The ears of the probe mounting structure 41 may be oriented such that an end of the probe is positionable outwardly from the end of the holder portion and may be easily directed by the user holding the device 10 toward a body part to be treated with energy emitted from the end of the probe.

The holder portion 12 may further comprise an engaging structure 42 that is configured to lock a position of the movable element with respect to the base element, the engaging structure having a locked condition and a released condition. The released condition may be characterized by the movable element 20 being substantially freely pivotable with respect to the mounting element 16. The locked condition may be characterized by the movable element not being pivotable with respect to the mounting element. In some illustrative embodiments, the engaging structure 42 may comprise a plurality of detents 44 formed on a first one of the mounting element and the movable element, and in the illustrative embodiments that detents are formed on the movable element but could be formed on the mounting element. Each of the detents 44 may be located a substantially equal distance from the pivot axis 22

The engaging structure 42 may further comprise a detent-engaging element 46 that is configured to engage one of the detents 44. The detent-engaging element 46 may be mounted on a second one of the mounting element and the movable element, and in the illustrative embodiments is mounted on the mounting element but could be formed on the movable element. The detent-engaging element 46 may be alignable with each of the detents by pivoting the movable element 20 with respect to the mounting element 16, and the element 46 may be selectively extendable into the one of the detents that is aligned with the detent-engaging element 46 to lock a corresponding position of the movable element with respect to the mounting element. The detent-engaging element 46 may be biased toward engagement with one of the detents, such as by spring loading or other means. In some embodiments, the detent-engaging element 46 may have a grip 48 or knob for permitting the hand of a user to push the detent-engaging element 46 out of engagement with the aligned detent, to thereby permit pivoting or rotation of the movable element with respect to the mounting element for changing the relative orientation of the movable element with respect to the mounting element, and any handle portion mounted on the mounting element.

The handle portion 14 of the reach extending device 10 may be form a socket 50 for receiving the mounting element of the handle portion. The bayonet structure 18 of the mounting element 16 of the handle portion may thus be removably received in the socket 50 to form a connection between the handle portion 14 and the holder portion 12. The handle portion 14 may including at least two sections, and may include a base section 52 and at least one extension section 54 that is extendable from the base section 52. The extension section 54 may be telescopically received inside the base section 52, and may be movable between a retracted position (see FIG. 1) and an extended position (see FIG. 2). Although the illustrative embodiments include a single extension section, more than one extension section may be mounted on the base section, such as in a telescoping manner, and it should also be recognized that the handle portion may also only include the base section without any extendable extension sections. Further, although the illustrative embodiments depict only one pivotable joint located between the mounting portion and the movable portion, more than one pivot joint may be utilized and may be positioned between various sections of the handle portion in addition to, or alternatively with, the pivot joint located between the handle portion and the holder portion.

The handle portion 14 may also include a locking structure 56 that is configured to selectively lock the extension section 54 in the extended position with respect to the base section 52. The locking structure 56 may be mounted on the base section 52. The locking structure 56 may comprise a collar 58 on the base section, and the collar may be located toward a distal end 60 of the base section. The extension section 54 may extend through at least a portion of the collar 58, and the collar 58 may define an aperture 62 through which a portion of the extension section is accessible. The locking structure 42 may further comprise a lock member 64 configured for selectively engaging the extension section 54 to resist movement of the extension section with respect to the base section 52. The lock member 64 may be movable between an engage position and a disengage position. The lock member 64 may be mounted on the collar 58. A portion of the lock member 64 may extend into the aperture 62 to engage the extension section 54 when the lock member 64 is in the engage position, and may engage a feature or structure on the exterior surface of the extension section such as a detent. Optionally, a series of detents may be formed in the exterior surface of the extension section at spaced locations to provide various points of engagement for the lock member at various degrees of extension of the extension section between the retracts position and the fully extended position. In some illustrative embodiments, the lock member 64 may comprise a rocker arm that is pivotally mounted on the collar 58 to pivot between the engage and disengage positions, and may be responsive to finger pressure applied to one end of the rocker arm to move the opposite end of the rocker arm into and out of engagement with the extension section. In some embodiments, the rocker arm may be biased into engagement with the extension section when finger pressure is not applied to the rocker arm to release the rocker arm from engagement with the extension section. It should be recognized that this locking structure is merely illustrative of locking structures that may have similar function and could be utilized on the device 10.

With respect to the above description then, it is to be realized that the optimum dimensional relationships for the parts of the invention, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:

1. A reach extending device for extending the reach and effective positioning of a therapy device, the reach extending device comprising:
    a holder portion configured to grip the therapy device and a handle portion releasably mounted on the holder portion;
    wherein the holder portion comprises a mounting element removably mountable on the handle portion, and a movable element for removably mounting on the therapy device, the movable element being movably mounted on the mounting element to permit movement of the movable element with respect to the handle portion; and
    wherein the handle portion comprises at least two sections, including a base section and at least one extension section extendable from the base section, the at least one extension section being movable between a retracted position and an extended position.

2. The device of claim 1 wherein the handle portion further comprises a locking structure configured to selectively lock the at least one extension section in the extended position with respect to the base section.

3. The device of claim 1 wherein the mounting element of the holder portion forms a bayonet structure, and the handle portion forms a socket for removably receiving the mounting element of the handle portion.

4. The device of claim 1 wherein the movable element includes a pair of opposed elements that are positionable on opposite sides of a housing of the therapy device.

5. The device of claim 4 wherein the opposed elements are spaced from each other and define a gap for receiving the therapy device.

6. The device of claim 5 wherein the pair of opposed elements include a first arm and a second arm forming a substantially U-shaped structure.

7. The device of claim 4 wherein the movable element includes a retaining loop element positionable about the opposed elements, the retaining loop having a securing position and a release position, the securing position being characterized by the retaining loop element engaging the opposed elements to restrict movement of the opposed elements away from each other to hold a therapy device therebetween, the release position allowing the opposed elements to move away from each other to release the therapy device.

8. The device of claim 1 wherein the holder portion comprises an engaging structure configured to releasably lock a position of the movable element with respect to the mounting element.

9. A therapy system, comprising:
    a therapy device having a housing with a first end and a second end; and
    a reach extending device comprising a holder portion receiving at least a portion of the housing of the therapy device, and a handle portion releasably mounted on the holder portion;
    wherein the holder portion comprises a mounting element removably mountable on the handle portion, and a movable element removably receiving the therapy device, the movable element being movably mounted on the mounting element to permit movement of the therapy device with respect to the handle portion; and wherein the handle portion comprises at least two sections, including a base section and at least one extension section extendable from the base section, the at least one extension section being movable between a retracted position and an extended position.

10. The system of claim 9 wherein the handle portion further comprises a locking structure configured to selectively lock the at least one extension section in the extended position with respect to the base section.

11. The system of claim 9 wherein the mounting element of the holder portion forms a bayonet structure, and the handle portion forms a socket for removably receiving the mounting element of the handle portion.

12. The system of claim 9 wherein the movable element includes a pair of opposed elements that are positioned on opposite sides of the housing of the therapy device.

13. The system of claim 12 wherein the opposed elements are spaced from each other and define a gap for receiving the therapy device.

14. The system of claim 12 wherein the pair of opposed elements include a first arm and a second arm forming a substantially U-shaped structure.

15. The system of claim 12 wherein the movable element includes a retaining loop element positionable about the opposed elements, the retaining loop having a securing position and a release position, the securing position being characterized by the retaining loop element engaging the opposed elements to restrict movement of the opposed elements away from each other to hold the therapy device therebetween, the release position allowing the opposed elements to move away from each other to release the therapy device.

16. A reach extending device for extending the reach and effective positioning of a therapy device, the reach extending device comprising:

a holder portion configured to grip the therapy device and a handle portion releasably mounted on the holder portion;

wherein the holder portion comprises a mounting element removably mountable on the handle portion, and a movable element for removably mounting on the therapy device, the movable element being movably mounted on the mounting element to permit movement of the movable element with respect to the handle portion;

wherein the handle portion comprises at least two sections, including a base section and at least one extension section extendable from the base section, the at least one extension section being movable between a retracted position and an extended position; and wherein the holder portion comprises an engaging structure configured to releasably lock a position of the movable element with respect to the mounting element.

17. The device of claim 16 wherein the handle portion further comprises a locking structure configured to selectively lock the at least one extension section in the extended position with respect to the base section.

18. The device of claim 16 wherein the movable element comprises:

a pair of opposed elements that are positionable on opposite sides of a housing of the therapy device; and a retaining loop element positionable about the opposed elements, the retaining loop having a securing position and a release position, the securing position being characterized by the retaining loop element engaging the opposed elements to restrict movement of the opposed elements away from each other to hold a therapy device therebetween, the release position allowing the opposed elements to move away from each other to release the therapy device.

\* \* \* \* \*